(12) United States Patent
Esener et al.

(10) Patent No.: US 11,357,830 B2
(45) Date of Patent: Jun. 14, 2022

(54) NANO-SCALE DELIVERY DEVICE AND USES THEREOF

(71) Applicants: The Regents of the University of California, Oakland, CA (US); Trogenex, Inc., Solana Beach, CA (US)

(72) Inventors: Sadik Esener, Solana Beach, CA (US); Negin Mokhtari, San Diego, CA (US); Mukanth Vaidyanathan, San Diego, CA (US); Ya-San Yeh, San Diego, CA (US); Ajay Sapre, La Jolla, CA (US); Bartu Ahiska, San Diego, CA (US)

(73) Assignees: THE REGENTS OF THE UNIVERSITY OF CALIFORNIA, Oakland, CA (US); TROGENEX, INC., Portland, OR (US)

( * ) Notice: Subject to any disclaimer, the term of this patent is extended or adjusted under 35 U.S.C. 154(b) by 0 days.

(21) Appl. No.: 15/449,830

(22) Filed: Mar. 3, 2017

(65) Prior Publication Data
US 2017/0252413 A1 Sep. 7, 2017

Related U.S. Application Data

(60) Provisional application No. 62/302,958, filed on Mar. 3, 2016.

(51) Int. Cl.
| | | |
|---|---|---|
| A61K 38/43 | (2006.01) | |
| A61K 9/51 | (2006.01) | |
| A61K 35/76 | (2015.01) | |
| B82Y 5/00 | (2011.01) | |

(52) U.S. Cl.
CPC ............ *A61K 38/43* (2013.01); *A61K 9/5115* (2013.01); *A61K 35/76* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 8,709,483 B2 * | 4/2014 | Farokhzad | A61K 9/5153 424/489 |
| 2015/0359871 A1 | 12/2015 | Stedman et al. | |
| 2015/0374798 A1 | 12/2015 | Labhasetwar et al. | |

FOREIGN PATENT DOCUMENTS

WO 2014124142 A2 8/2014

OTHER PUBLICATIONS

Quesasa et al (Hybrid PLGA-Organosilica Nanoparticles with Redox-Sensitive Molecular Gates. Chem. Mater., 2013, 25 (13), pp. 2597-2602) (Year: 2013).*
Sailor et al (Hybrid Nanoparticles for Detection and Treatment of Cancer. Adv Mater. Jul. 24, 2012; 24(28): 3779-3802). (Year: 2012).*
Lin et (Chem Mater. 2005, 17, 4570-4573). (Year: 2005).*
Zhang et al (Encapsulation of enzymes in silica nanocapsules formed by an amphiphilic precursor polymer in water. J. Mater. Chem. B, 2015, 3, 1261) (Year: 2015).*
Li et al (Liposomes as Protective Capsules for Active Silica Sol-Gel Biocomposite Synthesis. J. Am. Chem. Soc. 2005, 127, 37, 12756-12757) (Year: 2005).*
Dwivedi et al (Silica-Coated Liposomes for Insulin Delivery. Journal of Nanomaterials. vol. 2010, Article ID 652048, 8 pages (2010)). (Year: 2010).*
Wang et al (Delivery of Oligonucleotides with Lipid Nanoparticles. Adv Drug Deliv Rev. Jun. 29, 2015; 87: 68-80) (Year: 2015).*
Darbandi, M. et al., "Hollow Silica Nanospheres: In situ, Semi-In situ, and Two-Step Synthesis", Chem. Mater., 2007, 19(7), pp. 1700-1703.
Govender et al., "PLGA nanoparticles prepared by nanoprecipitation: drug loading and release studies of a water soluble drug", Journal of Controlled Release, 57, 1999, pp. 171-185.
Im, et al., "Polymer hollow particles with controllable holes in their surfaces", Nature Materials 4, 2005, pp. 671-675.
Kim, J.W. et al., "Cobalt oxide hollow nanoparticles derived by bio-templating", Chem Commun (Camb), Aug. 28, 2005, 32, pp. 4101-4103.
Liang, Z. et al., "Gold Nanoparticle-Based Core-Shell and Hollow Spheres and Ordered Assemblies Thereof", Chem. Mater., 2003, 15 (16), pp. 3176-3183.
Lim, Y.T. et al., "Multifunctional Silica Nanocapsule with a Single Surface Hole", Small. Mar. 2009, 5(3), pp. 324-328.
Ma et al., "Microwave-assisted hydrothermal synthesis and characterizations of PrF3 hollow nanoparticles", Mater Lett., 2007, 61(13), pp. 2765-2768.
Mohanraj, V.J. et al., "Silica nanoparticle coated liposomes: A new type of hybrid nanocapsule for proteins", International Journal of Pharmaceutics 392, 2010, pp. 285-293.
Nakamura, R. et al., "Shrinking of hollow Cu2O and NiO nanoparticles at high temperatures", Acta Materialia, Oct. 2008, 56(18), pp. 5276-5284.
Ortac et al., "Dual-Porosity Hollow Nanoparticles for the Immunoprotection and Delivery of Nonhuman Enzymes", Nano Letters, 2014, 14, pp. 3023-3032.

(Continued)

*Primary Examiner* — Jake M Vu
(74) *Attorney, Agent, or Firm* — Perkins Coie LLP

(57) ABSTRACT

Disclosed is a delivery device for delivering a payload, including a biological, chemical or biochemical substance, to a subject. The delivery device has a nanoparticle loaded with the payload, and porous coating structure over the loaded nanoparticle to prevent the payload from escaping the delivery device, while also preserving the activity of the payload and increasing effective utilization of the payload. Also disclosed is a delivery device for delivering a payload, including a natural virus, recombinant virus, or engineered virus. Also disclosed is a delivery device that has a liposome loaded with the payload and a biocompatible surface coating over the loaded liposome. Also disclosed are methods of fabricating the delivery devices and methods of using the delivery devices in treating health conditions, such as cancer, or in diagnostic applications.

15 Claims, 13 Drawing Sheets

(56) References Cited

OTHER PUBLICATIONS

Singhal et al., "Nanoparticle-mediated catalase delivery protects human neurons from oxidative stress", Cell Death and Disease (2013) 4, e903.
Son et al., "Porous calcium phosphate granules containing drug-loaded polymeric nanoparticles for bone regeneration", Mater Lett. 2012, 76, pp. 243-246.
Veronese, F.M., "Peptide and protein PEGylation: a review of problems and solutions", Biomaterials 22, 2001, pp. 407-417.
Wang, B. et al., "Preparation and cellular uptake of PLGA particles loaded with lamivudine", Chin Sci Bull. 2012, 57, pp. 3985-3993.
Wu et al., "Sustained delivery of endostatin improves the efficacy of therapy in Lewis lung cancer model", J. Control. Release 2009:134, pp. 91-97.
Yang, J. et al., "Hollow Silica Nanocontainers as Drug Delivery Vehicles", Langmuir, 2008, 24 (7), pp. 3417-3421.
Yang, J. et al., "Synthesis of Hollow Silica and Titania Nanospheres", Chem. Mater., 2008, 20 (9), pp. 2875-2877.

\* cited by examiner

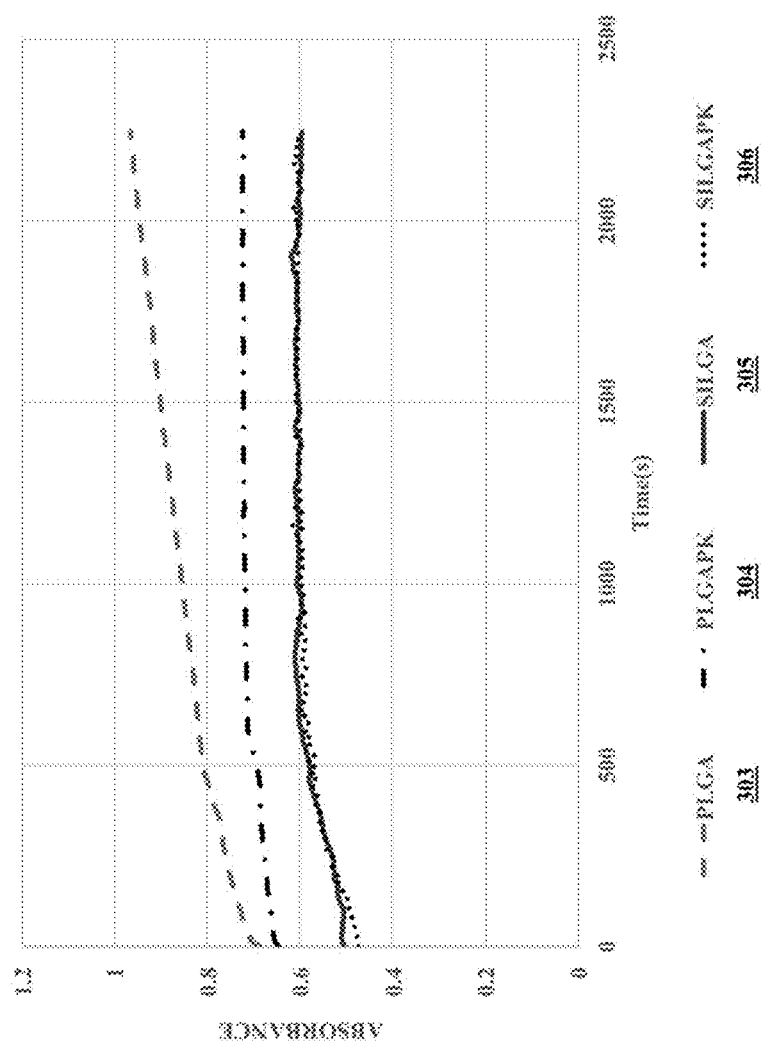

NANO-SCALE DELIVERY DEVICE AND USES THEREOF

CROSS-REFERENCE TO RELATED APPLICATION(S)

This patent document claims benefit and priority of U.S. Provisional Patent Application No. 62/302,958 entitled "NANO-SCALE DELIVERY DEVICE AND APPLICATIONS THEREOF," filed on Mar. 3, 2016. The entire content of the aforementioned patent application is incorporated by reference as part of the disclosure of this patent document.

TECHNICAL FIELD

This patent document relates to systems, devices, and processes that use nanotechnology for delivering a biological, chemical or biochemical substance to a subject.

BACKGROUND

In various instances, it may be desirable or beneficial to modulate the lifetime and behavior of drugs, therapeutics, diagnostic probes, or other substances administered into the body. Such modulations may, for example, facilitate an anti-cancer drug to reach a target tumor in greater numbers than alternative medicines, while limiting systemic toxicity to leave healthy cells unharmed.

Currently available methods attempt to deliver a payload by chemically or electrostatically binding materials to the payload. These binding methods are applicable to only a limited range of payloads (e.g. because the payload must be capable of binding in a predetermined manner), are ineffective in offering preservation (e.g. because the material has significant/residual/partial toxicity or immunogenicity, or degrades in an undesirable manner), are complex to bulk manufacture, and/or wholly or substantially block any activity of an active payload (e.g. the binding and/or material affects delivery efficiency or activity of the payload). The technology and devices disclosed herein, among other benefits, overcome these limitations in the field.

SUMMARY

In one aspect, disclosed herein is a delivery device for delivering to a subject a payload while preserving the lifetime and/or activity of the payload. The delivery device includes a nanoparticle loaded with the payload; and a biocompatible coating encapsulating the nanoparticle, wherein the payload is prevented from traversing out of the delivery device. The payload is a biological, chemical or biochemical substance, or a combination thereof. In some embodiments, the payload is an active payload (or active substance), which is a biological, chemical or biochemical substance that has an effect, e.g., a biological and/or a therapeutic effect, and/or interaction with an imaging or diagnostics modality. Examples of an active payload include but are not limited to a drug, vaccine, preventative, adjuvant, enzyme, cofactor, virus, nucleic acid, antigen, imaging or contrast agent, radioactive tracer or a combination thereof. In some embodiments, the payload is a bioactive payload (or bioactive substance), which is a biological, chemical or biochemical substance that has biological effects. In some embodiments, the payload is covalently or non-covalently bound to the nanoparticle. In some embodiments, the payload is not bound to the nanoparticle. In some embodiments, the delivery device comprises a porous coating such that the payload is in contact or selective contact with the surrounding environment, e.g. with small substances (e.g. small molecules) that can traverse the pores, but not larger substances (e.g. immune system components such as antibodies and white blood cells). In some embodiments, the delivery device comprises a non-porous coating such that the payload is not in contact with the surrounding environment until the payload is released from the delivery device. In some embodiments, the delivery device further comprises one or more functionalized group, e.g., a targeting molecule to allow the delivery device to reach or avoid one or more specific target(s) in greater numbers.

In a related aspect, disclosed herein is a pharmaceutical composition comprising the delivery device loaded with a therapeutically effective amount of the payload. The pharmaceutical composition can further comprise a pharmaceutically acceptable carrier, excipient, diluent, preservative, surfactant, dispersing agent, stabilizer, solvent, emulsifier, or a combination thereof. Moreover, the pharmaceutical composition can be formulated into any desirable formulation depending on the administration route, including but not limited to oral administration, parenteral administration (e.g., intravenous administration, intramuscular administration, subcutaneous administration), etc.

In one aspect, disclosed herein is a method to deliver a payload to a subject while preserving the lifetime and/or activity of the payload, comprising the steps of: (i) forming a nanoparticle encapsulating a payload via an emulsion process, wherein the payload is not bound (e.g. chemically or electrostatically) to the nanoparticle; (ii) coating the nanoparticle with a biocompatible coating to form a delivery vehicle; and (iii) administering the delivery vehicle to the subject, wherein upon administration at least one of the following properties is enhanced relative to administering an uncoated nanoparticle: (a) preservation from cell-mediated or antibody immune response; (b) reduced toxicity; (c) prolonged half-life of the payload (e.g. in circulation, muscle, a tumor, etc.); (d) utilization of the payload, or (e) cellular uptake of the payload.

In another aspect, disclosed herein is a method to deliver and preserve activity of an active or bioactive payload in a subject comprising the steps of: (i) forming a nanoparticle encapsulating an active or bioactive payload via an emulsion process, wherein the active or bioactive payload is not bound to the nanoparticle; (ii) coating the nanoparticle with a biocompatible porous coating to form a delivery vehicle; and (iii) administering the delivery vehicle to the subject, wherein upon administration the active or bioactive payload is prevented from traversing the porous coating, and wherein at least one additional substance essential for the activity is permitted to traverse the porous coating to or from the active or bioactive payload, and wherein at least one of the following properties is enhanced relative to administering an uncoated nanoparticle: (a) preservation from cell-mediated or antibody immune response; (b) reduced toxicity; (c) prolonged half-life of the active or bioactive payload (e.g. in circulation, muscle, a tumor, etc.); or (d) utilization of the active or bioactive payload.

In another aspect, disclosed herein is a method and system wherein the activity of the active payload within the subject can be externally started or controlled (e.g. rate increased) due to properties of the delivery vehicle's nanoparticle and coating. For example, in some embodiments wherein the nanoparticle includes a liposome impermeable to the additional substance, ultrasound or sonication or vibrations at a certain frequency, intensity and/or time duration is applied to disrupt integrity of the liposome and permit traversal of the additional substance to or from the active payload (thereby a form of external control of the activity of the active payload), while the coating remains intact and preserves the payload.

In yet another aspect, disclosed herein is a method to deliver to a subject a payload while preserving the lifetime and/or activity of the payload, comprising multiple dependent or interacting components, including but not limited to cascading enzymes or multiple viruses.

In another aspect, disclosed herein is a method and system wherein the coating is functionalized to further enhance delivery and/or preservation of the delivery vehicle in a subject.

BRIEF DESCRIPTION OF THE DRAWINGS

FIG. 3C shows measurements of Beta Lactamase (BLA) activity when encapsulated in uncoated PLGA nanoparticle (303, 304) and in a delivery vehicle comprising silica coated PLGA nanoparticle (305, 306) in the absence and presence of Proteinase-K (PK).

DETAILED DESCRIPTION

Figure 1A:
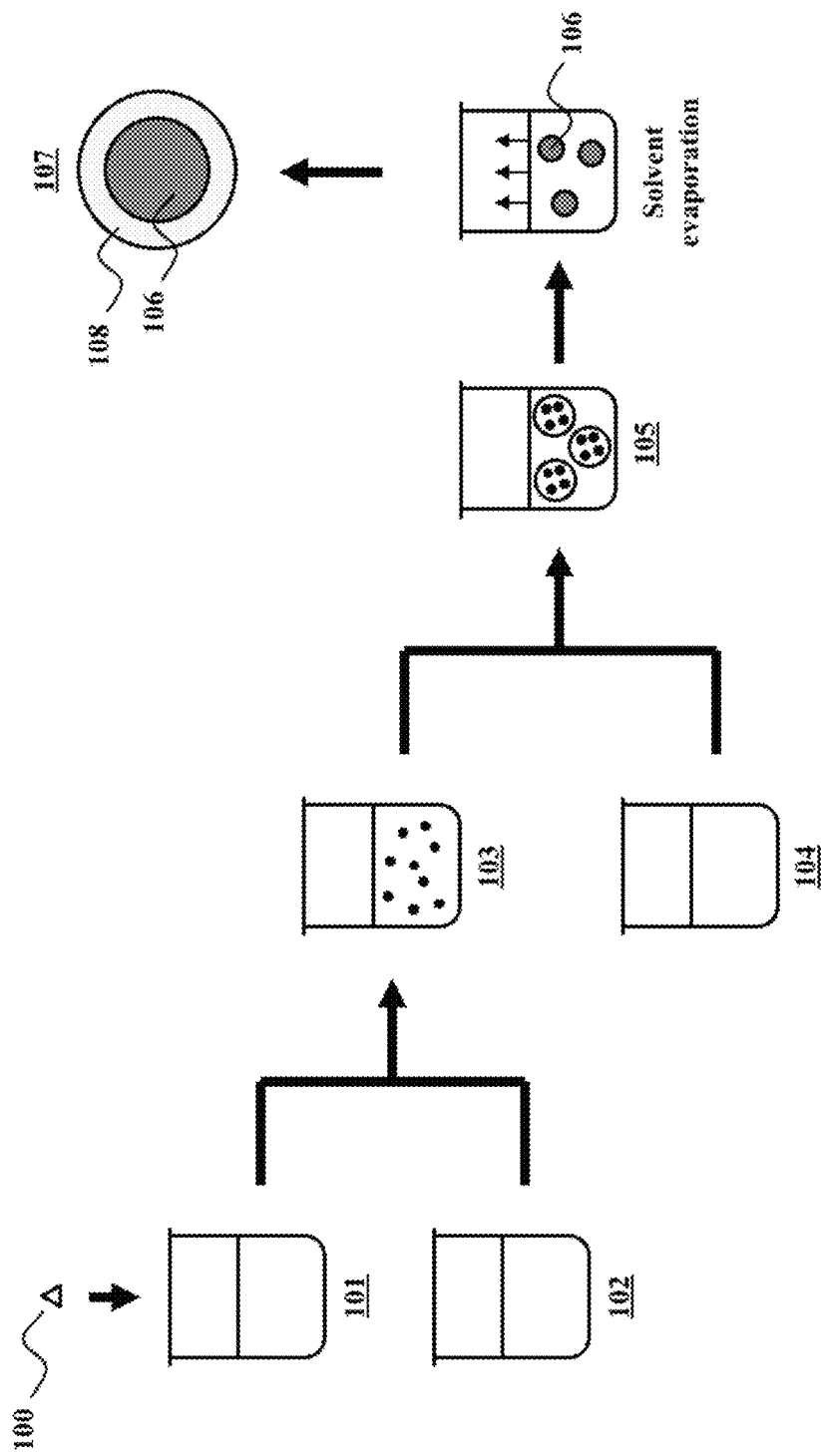
FIG. 1A shows an example of a method used for fabricating encapsulation of a payload (100), in accordance with an embodiment of the present disclosure.

The numerous innovative teachings of the present application will be described with particular reference to various embodiments (by way of example, and not of limitation). The present application describes several embodiments, and none of the statements below should be taken as limiting the scope of the claims generally.

Although methods and materials similar or equivalent to those described herein can be used in the practice or testing of the present disclosure, suitable methods and materials are described below. All publications, provisional patent applications, patent applications, patents, articles, publications, books, websites, and other referenced materials mentioned herein are incorporated by reference in their entirety. In the case of conflict, the present specification, including explanations of terms, will control. In addition, the materials, methods, systems, and examples are illustrative only and not intended to be limiting the inventions disclosed herein.

There are many instances in which it is desirable to modulate the lifetime and behavior of drugs, therapeutics, viruses, diagnostic probes, or other substances administered into the body. Such modulations may, for example, facilitate an anti-cancer drug to reach a target tumor in greater numbers than alternative medicines, while limiting systemic toxicity to leave healthy cells unharmed.

In one aspect, the present disclosure provides a system and method for the entrapment of an enzyme, virus or drug without modifying the enzyme, virus or drug itself, while extending its in vivo/circulation half-life, enhancing its utilization, modulating its immunogenicity, modulating its tropism, and/or providing a surface that can readily be functionalized with one or more specific targeting agents, or a combination thereof. This disclosure provides a platform that can be used for many applications in nanomedicine including but not limited to using nanoparticles as enzymes, viruses or drug delivery vehicles for therapeutic applications such as amino acid depletion therapy for cancerous tumors, antioxidant therapy for oxidative stress (e.g. in ischemia and reperfusion injury), Multiple Sclerosis, imaging (for example in the brain by using a fluorescent payload inside the delivery vehicles, or one or more quantum dots), biosensors, gene therapy, infectious disease, etc.

In one aspect, disclosed herein is the ability to deliver a payload in a delivery vehicle while preserving the lifetime and/or activity of the payload wherein the payload is loaded in a nanoparticle that does not require binding to the payload, combined with a nanoscale coating that enhances preservation and delivery properties of the payload and loaded nanoparticle in a subject. In some embodiments, also disclosed herein is the ability to preserve activity or externally trigger activity of an active or bioactive payload using this novel delivery vehicle. Furthermore, in some embodiments, also disclosed herein is the delivery of a combination of multiple dependent payloads using this novel delivery vehicle to achieve effects that cannot be achieved by delivery of each component payloads individually using alternative methods.

Protecting and Delivering a Payload

In one aspect, disclosed herein is a method to deliver a payload to a subject while preserving the lifetime and/or activity of the payload, comprising the steps of: (i) forming a nanoparticle encapsulating a payload, wherein the forming includes an emulsion process, and wherein the payload is not bound (e.g. chemically or electrostatically) to the nanoparticle; (ii) coating the nanoparticle with a biocompatible coating to form a delivery vehicle; and (iii) administering the delivery vehicle to the subject, wherein upon administration at least one of the following properties is enhanced relative to administering uncoated nanoparticle: (a) preservation from cell-mediated or antibody immune response; (b) reduced toxicity; (c) prolonged half-life of the payload (e.g. in circulation); (d) utilization of the payload, or (e) cellular uptake of the payload. In some embodiments, at least one of the above properties is enhanced relative to administering unencapsulated payload.

In some embodiments, the payload comprises a peptide, oligopeptide, polypeptide or protein, such as, for example but not limited to, an enzyme, or a combination thereof. In some embodiments, the payload comprises a nucleic acid, such as for example DNA, RNA, siRNA, or a combination thereof. Nucleic payloads can be used for numerous purposes, including for example but not limited to transformation or transfection of a host cell in the subject, modulated expression, gene silencing, RNA interference, or a combination thereof. In some embodiments, the payload comprises a protein and a stabilizing agent. In some embodiments, the payload comprises a virus, virus-like particle (VLP), a virus protein capsid, or any combination thereof. In some embodiments, the payload comprises a natural virus, recombinant virus, or engineered virus. In some embodiments, the payload comprises Adenovirus (ADV), Adeno-associated virus (AAV), Vaccinia Virus (VV), Herpes Simplex Virus (HSV), Coxsackievirus, Parvovirus, Reovirus, Seneca Valley Virus, Vesicular stomatitis virus, and/or Measles Virus. In some embodiments, the payload comprises an oncolytic virus that preferentially expresses in and/or preferentially lyses (breaks down) cancerous cells (or cells that express phenotypes associated with cancerous cells, including but not limited to increased metabolism or increased protein expression e.g. the folate receptor protein (FR) on the surface of many human cancers), such as, for example but not limited to, cells belonging to the following cancer types: bladder, brain, breast, cervix uteri, colorectum, corpus uteri (including endometrium), gallbladder, head & neck, kidney (including renal cell cancer), larynx, leukemia, lip, liver, lung (including bronchus), melanoma, multiple myeloma, nasopharynx, nervous system, non-Hodgkin lymphoma, oesophagus, oral cavity, ovary, pancreatic, pharynx, prostate, stomach, testis, thyroid cancer, cells with one or more defect(s) in the p53 pathway, or a combination thereof. Examples of these cells include but are not limited to cancerous epithelial cells (carcinoma), cancerous cells of the blood or lymphatic system (leukemia or lymphoma), and cancerous connective tissue cells (sarcoma). In some embodiments, the payload is a biologic, drug, therapeutic, antigen, adjuvant, diagnostic formulation, imaging probe (e.g. fluorescent marker, ultrasound contrast agent, quantum dot, or CT contrast agent), therapy sensitizers (e.g. ablative therapy sensitizer), or a combination thereof. In some embodiments, the payload is the enzyme catalase that converts toxic hydrogen peroxide to water and oxygen.

In some embodiments, the nanoparticle is loaded with the payload during the process of formation, or as an additional step after formation.

In some embodiments, the delivery vehicle or a pharmaceutical composition comprising the delivery vehicle is administered into a circulatory or extracellular system of the subject. In some embodiments, the administration is by subcutaneous injection, intratumoral injection, intramuscular injection, intravenous injection, other extracellular injection, or a combination thereof.

In some embodiments, the nanoparticle is formed using double-emulsion-solvent-evaporation (DESE). In one embodiment of the present disclosure, the DESE is a water-in-oil-in-water "w/o/w" method that is used to form polymeric nanoparticles of tunable size with a payload (once coated, the final particle size should be large enough to encapsulate sufficient payload, yet small enough that they do not cause biodistribution or toxicity problems in the subject, e.g. submicron or 10 nm-1000 nm). In some embodiments, the payload is incorporated with the first water phase prior to forming the nanoparticle using a technique known in the art (Singhal, A., Morris, V. B., Labhasetwar, V., & Ghorpade, A. (2013) "Nanoparticle-mediated catalase delivery protects human neurons from oxidative stress," Cell Death and Disease, 4(11) describes a w/o/w method). In some embodiments, an alternative DESE method is used, such as, for example but not limited to w/o/o, also known in the art (Wu, J., Ding, D., Ren, G., Xu, X., Yin, X., & Hu, Y. (2009) "Sustained delivery of endostatin improves the efficacy of therapy in Lewis lung cancer model," Journal of Controlled Release, 134(2), 91-97 describes a w/o/o method). In cases where the payload is comprised of proteins susceptible to denaturation or degradation, an appropriate emulsion method is chosen to mitigate this. In one embodiment of this disclosure, the polymer is poly(lactic-co-glycolic acid) (PLGA), or other biodegradable and/or biocompatible copolymer, such as, for example, poly(methyl methacrylate) (PMMA), and wherein fabrication of the polymeric nanoparticle or delivery vehicle does not reply upon any polymer binding upon the payload with electrostatic interaction. The degradation of polymeric nanoparticles formed using the process above varies from several days to even months. In some embodiments, isomeric poly(l-lactic acid) (PLLA) and/or poly(dl-lactic acid) (PDLA) are included with PLGA in the oil phase (e.g. 2:5 or 1:2 ratio of PLLA/PDLA to PLGA) to control the size, shape and/or homogeneity of the formed nanoparticles.

In some embodiments, the nanoparticle is formed using nano-precipitation (precipitation, solvent displacement). In some embodiments, nano-precipitation is chosen over an emulsion method due to loading efficiency and/or stability of at least portion of the payload. Known in the art is a nano-precipitation method for fabricating polymeric nanoparticles (Govender, T. (1999) "PLGA nanoparticles prepared by nanoprecipitation: drug loading and release studies of a water soluble drug," Journal of Controlled Release, 57(2), 171-185 describes a nano-precipitation method). In some embodiments of the present disclosure, the payload is coupled to the surface of a polymeric particle formed using nano-precipitation, and then coated (e.g. with silica, calcium phosphate or titanium oxide) to form the delivery vehicle.

In some embodiments, the nanoparticle is coated with a porous, selectively permeable or semi-permeable layer, for example with a pore size that permits small molecules below a given size to pass, but rejects larger molecules (size could be, for example, as measured in nanometers (nm), Daltons (Da) or atomic mass units (u)). In one embodiment, the porous coating is a nanoscale layer of Silicon Dioxide (silica) applied using a sol-gel chemistry at a nanoscale thickness that permits small molecules to pass (e.g. silica with an average pore size of 1-9 nm). The pore size and shape when coating with silica can be controlled in range 1-80 nm, e.g. by controlling catalysts and preparation conditions (e.g. the pH value). In some embodiments, the surface coating is an inorganic material or colloidal metal, for example, titanium oxide, calcium phosphate, alginate, calcium alginate, other material with sufficient biocompatibility, or a combination thereof. In some embodiments, the surface coating is composed of approximately 20%, 30%, 40%, 50%, 60%, 70%, 80%, 90% or 100% of silica, titanium dioxide, calcium phosphate, alginate, calcium alginate or a colloidal metal. In some embodiments, the silica is in amorphous or liquid silica form. In one embodiment, the process of coating the nanoparticle produces a high yield of coated particles. In some embodiments, the coating process produces a yield of approximately 20%, 30%, 40%, 50%, 60%, 70%, 80%, 90% or 100% coated particles, with the remaining particles uncoated, partially coated, destroyed, or any combination thereof. In some embodiments, the coating process is readily scaled to an industrial scale without significantly compromising the desired properties of the nanoscale coating (for example, but not limited to, thickness, consistency, purity, shape, surface area, durability, curvature, roughness, variability, charge, disposition to aggregate, or propensity for functionalization). In one embodiment, the coating gives the nanoparticle a biodistribution and toxicology that is well tolerated by the subject, and/or is eventually excreted or biodegraded.

In some embodiments, the encapsulation method yields a payload loading efficiency of approximately 20%, 30%, 40%, 50%, 60%, 70%, 80%, 90% or 100%.

In some embodiments, the payload is encapsulated within the delivery vehicle above to modulate any one or more of: (i) propensity for immune inhibition by neutralizing antibodies or a cellular immune response, immunogenicity and/or antigenicity, (ii) a controlled and/or sustained payload release profile, (iii) payload toxicity, (iv) payload utilization, (v) payload tropism, (vi) targeting, for example by surface functionalization or magnetic guidance, (vii) uptake by target cell type, cell line, organelle, tissue, organ or system, or (viii) route of administration. In one embodiment of the present disclosure, a delivery vehicle comprising a silica coated polymeric nanoparticle results in a reduction (e.g. a measurable reduction) in immune inhibition of a payload (e.g. a reduction in antibodies specific to the payload in a blood sample) and increases the payload's circulation time (e.g. from seconds or a few minutes to hours, days or weeks). In some embodiments, the nanoparticle alone is unable or insufficient in modulating one or more of such properties, and the coating is therefore required for the desired behavior. In some embodiments, accumulation of the payload within one or more target cell types, tissues, or organs is greater via coated nanoparticle than with uncoated nanoparticle.

In some embodiments, the surface of the delivery vehicle is functionalized with targeting agents for targeted therapy, and/or with PEG to, for example but not limited to, increase circulation time or modify tropism. For surface functionalization, options beside PEG, like unmodified or modified sugar, proteins, antibodies, nucleic acids, fatty acids, saturated and unsaturated fats, lipids, 3-aminopropyl triethoxysilane (ATPS), 3-mercaptopropyl trimethoxysilane (MPTS), etc. may be used. In some embodiments wherein the coating is comprised of silica, surface functionalization is achieved by reaction with an alkoxysilane/halosilane.

In some embodiments, the biocompatible coating layer prevents interaction of the payload or nanoparticle with components of the subject's immune system, such as immune cells, neutralizing antibodies or a combination thereof. In some embodiments, the coating is degraded by an higher acidity (lower pH) environment upon being internalized by a cell (e.g. by endocytosis), such as, for example, within an intracellular vesicle (e.g. an endosome).

FIG. 1A shows an example of a method that was used for encapsulating payload (100), in accordance with an embodiment of the present disclosure. In this example, payload (100) was a combination of (i) the enzyme bovine catalase, and (ii) rat serum albumin (RSA) to protect the enzyme during encapsulation. An internal aqueous phase (101) was prepared by forming a solution of payload (100) in water. An organic phase (102) was prepared by dissolving a polymer into an organic solvent. In this example, organic phase (102) was polymer PLGA in organic solvent dichloromethane (DCM). In some embodiments, organic phase (102) additionally comprises of a plasticizer, such as, for example but not limited to, diethyl tartrate (DMT). Internal aqueous phase (101) was then added to (emulsified in) organic phase (102) to create primary emulsion (103), while vortexing and/or sonication (or vice versa). In this example, the mixture was created while vortexing and afterwards probe-sonication on ice. An external aqueous phase (104) was prepared by forming a solution of an emulsifier (or surfactant) in water. An emulsifier was used to reduce the surface tension and stabilize the droplet phase during the emulsification process. In this example, external aqueous phase (104) was 5% polyvinyl alcohol (PVA) in water, where the PVA acted as an emulsifier. Primary emulsion (103) was then added to external aqueous phase (104) to create secondary emulsion (105). In this example, secondary emulsion (105) was vortexed and probe-sonicated on ice. The organic solvent, in this case DCM, was allowed to evaporate and polymeric particles (106) harden. In this example, the DCM was evaporated overnight at room temperature. Polymeric particles (106) were then vacuum dried (in this case for one hour), collected by centrifugation, and washed (in this case three times) with water to remove any excess PVA. In some embodiments, polymeric particles (106) are washed, centrifuged, and then lyophilized for long term storage. Delivery vehicles (107) were then formed by coating polymeric particles (106) with surface coating (108). In this example, polymeric particles (106) were coated with silica for four hours (in this case using method (iii) below). In some embodiments, the silica coating is coated by combinations such as, for example but not limited to: (i) a 0.75:1.5 ratio of (3-aminopropyl) trimethoxysilane (APTMS) and tetramethyl orthosilicate (TMOS) in ethanol or water; (ii) TMOS in ethanol or water; (iii) silicic acid (a ratio of 75:1000 TMOS and HCL) in 1×PBS (phosphate-buffered saline) or water; or (iv) silicic acid (a ratio of 75:1000 TMOS and HCL) and poly-L-lysine (PLL) in 1×PBS or water (e.g. in an embodiment PLL adds positive charge to the nanoparticle to assist formation of silica coating).

In an embodiment of the present disclosure, carboxyl or ester terminated (capped) PLGA is used for the polymeric particles. These are coated with silica for a duration of time (for example 4 hours), resulting in a measurable increase in particle size, increase in the PDI, and more negative charge. In one embodiment, the negative charge as well as the presence of carboxyl (or carboxyl acid, or carboxylic acid) and PVA prevents the particles from aggregation. In some embodiments, additional steps are taken to minimize particle aggregation, for example but not limited to: (a) probe sonicating the resulting delivery vehicle suspension, and/or (b) adding all or at least one of the reagents in a dropwise fashion while shaking, or while stirring on a hotplate.

In some embodiments, the poly(lactic-co-glycolic acid) (PLGA) comprises of an approximately 50:50 ratio of lactic to glycolic acid ratio. In some embodiments, a higher lactic to glycolic acid ratio is used, for example 60:40 ratio. In some embodiments a lower lactic to glycolic acid ratio to result in a PLGA that hydrolyzes (breaks down with water) faster, for example a 40:60 or 25:75 ratio. This may be desirable in applications wherein the diffusion rate of small molecules from the outside of the delivery vehicle to the payload is important. In one embodiment of the present disclosure, the polymer is biodegradable and degrades over time in water or biological conditions. The degradation of the polymer increases biological activity of the enzyme payload because of increased diffusion of substrates (reactants) and/or products (e.g. the resulting from a substrate binding to the enzyme) from/to the enzyme. The enzyme remains protected by the surface coating. In some embodiments, the degradation of the polymer is accelerated by external intervention. In some embodiments, the composition of the PLGA and coating is chosen to result in a controlled release of the payload when administered into a subject.

In some embodiments of the present disclosure, the payload is coupled to the surface of the nanoparticle. Referring to FIG. 1A, in some embodiments payload (100) is coupled to the surface of polymeric particle (106) (which was formed without payload (100) inside), and then coated with surface coating (108) to form delivery vehicle (107).

In some embodiments, the delivery device further has a targeting agent on the surface for targeted delivery of the device to or away from one or more sites in the subject, such as for example but not limited to antibodies, folic acid, polyethylene glycol (PEG) or a combination thereof. In certain embodiments, the delivery device further has a functionalization agent on the surface for modulating the in vivo or circulation half-life of the device, such as for example but not limited to polyethylene glycol (PEG).

In some embodiments of the present patent document, variations to this fabrication method may be used depending on the specific payload and/or intended application. Examples of variations that can be modified include, but are not limited to: payload, chemicals, emulsifier concentration, particle size, silica coating time, sonication duration and/or power, PLL length, surface coating (108) surface modification or dopants, or a combination thereof.

Preserving Activity of an Active or Bioactive Payload

In one aspect, disclosed herein is a method to deliver and preserve activity of an active or bioactive payload in a subject comprising the steps of: (i) forming a nanoparticle encapsulating an active or bioactive payload, wherein the forming includes an emulsion process, and wherein the active or bioactive payload is not bound to the nanoparticle; (ii) coating the nanoparticle with a biocompatible porous coating to form a delivery vehicle; and (iii) administering the delivery vehicle to the subject, wherein upon administration the active or bioactive payload is prevented from traversing the porous coating, and wherein at least one additional substance essential for the activity is permitted to traverse the porous coating to or from the active or bioactive payload, and wherein at least one of the following properties is enhanced relative to administering uncoated nanoparticle: (a) preservation from cell-mediated or antibody immune response; (b) reduced toxicity; (c) half-life of the active or bioactive payload (e.g. in circulation); or (d) utilization of the active or bioactive payload.

In one embodiment of the present disclosure, the active or bioactive payload is active within the delivery vehicle following administration to the subject. The payload maintains substantially whole or at least partial function while encapsulated within the delivery vehicle. In some embodiments wherein the payload comprises an enzyme: (i) the enzyme is prevented from traversing out of the porous coating of the delivery vehicle, and (ii) the porous coating permits substrates of the enzyme to traverse into the delivery vehicle. Additionally, in some embodiments: (iii) the porous coating permits products of the enzyme to traverse out of the delivery vehicle. The enzyme is protected within a porous structure, and yet is able to maintain substantial functionality. In some embodiments, activity of the enzyme is sufficient for a therapeutic purpose despite a rate-limitation caused by the slow-down of substrates or products diffusing through the porous coating, polymeric nanoparticle, any other component of the delivery vehicle, or a combination thereof. In some embodiments the rate limiting step of the activity is the speed of the enzyme.

In one aspect, the present disclosure provides a method for the synthesis of a new type of loaded polymeric nanoparticle with a porous coating encapsulating one or more active or bioactive substances, for example enzymes. One advantage of the delivery device disclosed herein is that it allows the payload encapsulated in the nanoparticle to interact with small molecules in the surrounding environment. Due to the small size, these small molecules can penetrate the porous coating of the nanoparticle thereby having a direct contact with the payload. On the other hand, the payload has a large enough size relative to the pore size of the coating such that the payload remains encapsulated within the nanoparticle. Thus, the payload inside the coated delivery vehicle is protected from the immune system by the porous coating (e.g., a silica layer), in accordance with an embodiment of this patent document. In one embodiment, the blood circulation time of the enzyme(s) is prolonged due to the small size of the delivery vehicle, and its fabrication from inert, FDA-approved materials. In some embodiments, the surface-coating protects the payload from in vivo inactivation from, such us, for example but not limited to, cofactor-loss. Cofactors (e.g. metal ions, coenzymes) are substances that assist the biological activity of proteins, for example assist enzymes during catalysis. In some embodiments, the payload includes one or more cofactors that are encapsulated within the delivery vehicle together with related one or more enzymes.

Referring to FIG. 1A, in one embodiment silica coating (108) has pores large enough for small molecules to sufficiently pass (e.g. substrate (hydrogen peroxide) and products (water, oxygen) of catalase), while also small enough such that payload (100) (e.g. catalase) cannot exit. Payload (100) is therefore effectively caged within delivery vehicle (107).

Payload (100) used in this example was the enzyme catalase, consistent with an embodiment of the present disclosure. Catalase is used to convert toxic hydrogen peroxide in the body to water an oxygen. While catalase is protected inside delivery vehicle (107) from immune inhibition, small hydrogen peroxide molecules can diffuse inside across the porous coating (108) and get converted to harmless water and oxygen products.

Other examples of a payloads encapsulated according to the current disclosure are choline oxidase or glucose oxidase (GOx). In one embodiment of the present disclosure, the bioactive payload has higher activity at locations within the subject that have upregulated substrate, or in other ways high concentrations of substrate. For example but not limited to, increased GOx activity in a tumor microenvironment with increase glucose.

Figure 1B:
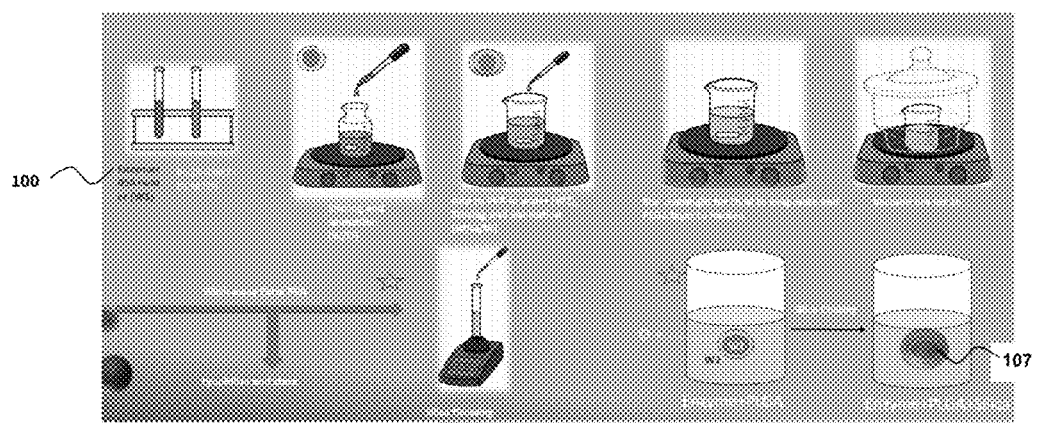
FIG. 1B shows an example of a method used for fabricating encapsulation of an enzyme and RSA payload (100) to form a delivery vehicle (107) comprised of a silica coated loaded nanoparticle using a PLGA polymer, in accordance with an embodiment of the present disclosure.

FIG. 1B shows an example of a method that was used to encapsulate enzyme and RSA payload (100) to form delivery vehicle (107) using a PLGA polymer, in accordance with an embodiment of this patent document. There are several synthesis protocols for this kind of fabrication approach. One of the synthesis protocols is described below where the enzyme catalase is loaded inside PLGA nanoparticles and then coated with a porous silica layer using a sol-gel chemistry.

In the first step of synthesis the PLGA nanoparticles were used as a stepping stone to encapsulate the payload inside and/or on it using double emulsion solvent evaporation (DESE) method (Singhal, A., Morris, V. B., Labhasetwar, V., & Ghorpade, A. (2013) "Nanoparticle-mediated catalase delivery protects human neurons from oxidative stress," Cell Death and Disease, 4(11) describes a DESE method) and afterwards the entire nanoparticle was sealed with a porous silica layer (FIG. 1B). Here, bovine Catalase and Rat Serum Albumin (RSA) in water were used as initial water phase (W1). RSA protects the enzyme during the encapsulation process. The W1 mixture was then added to PLGA in DCM and DMT while vortexing and afterwards probe sonication on ice. Here DCM was used as the organic solvent and DMT as a plasticizer (in some embodiments this is omitted). The mixture was then added to a solution of 5% PVA in water, making this the second water phase (W2). PVA acts as an emulsifier. The mixture was vortexed and probe sonicated on ice and the solvent (DCM) was evaporated overnight at room temperature, while also allowing the PLGA nanoparticles to harden. The mixture was then vacuum dried for 1 hour and centrifuged and washed 3 times with water to remove any excess PVA. The (w/o/w) nanoparticles were then coated with silica for 4 hours. Depending on the nanoparticle charge silica is coated on the PLGA nanoparticles by combinations like: a ratio of 0.75:1.5 APTMS and TMOS in Ethanol (or water), TMOS in Ethanol (or water), Silicic Acid (a ratio of 75:1000 TMOS and HCL) in 1×PBS (or water), Silicic Acid (a ratio of 75:1000 TMOS and HCL) and PLL in 1×PBS (or water).

The silica shell has pores allowing small molecules to pass through. However, the payload cannot pass through the pores, therefore it is sealed within the delivery vehicle. In some embodiments, there are variations to this fabrication approach, for example PLGA size or payload, silica coating time, probe sonication duration and power, PLL length, and a combination thereof. In some embodiments, short PLL molecules are used to reduce particle aggregation.

Figure 8:
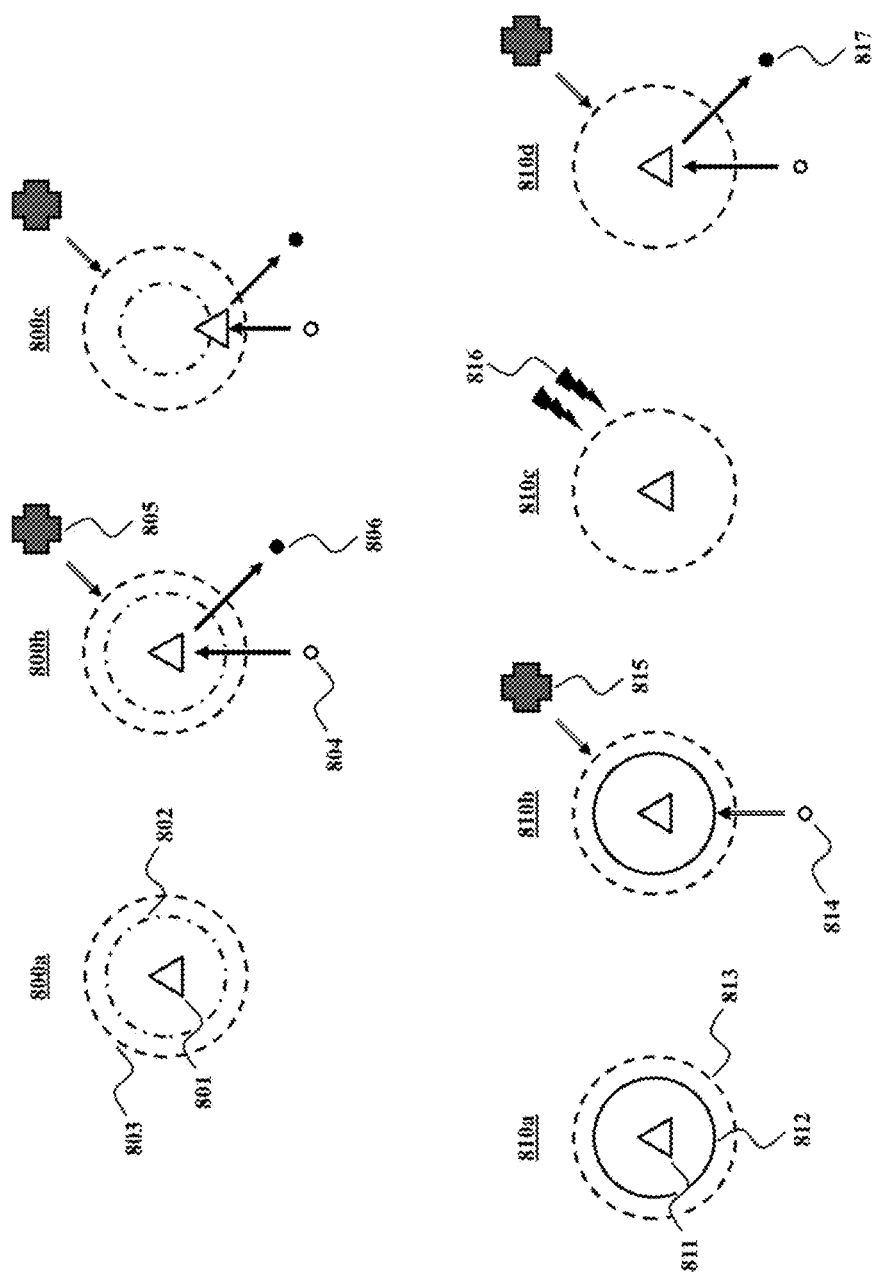
FIG. 8 shows examples of payloads (801, 811) within delivery vehicles (800a-c, 810a-d) in accordance with some embodiments of the present disclosure.
Figure 9:
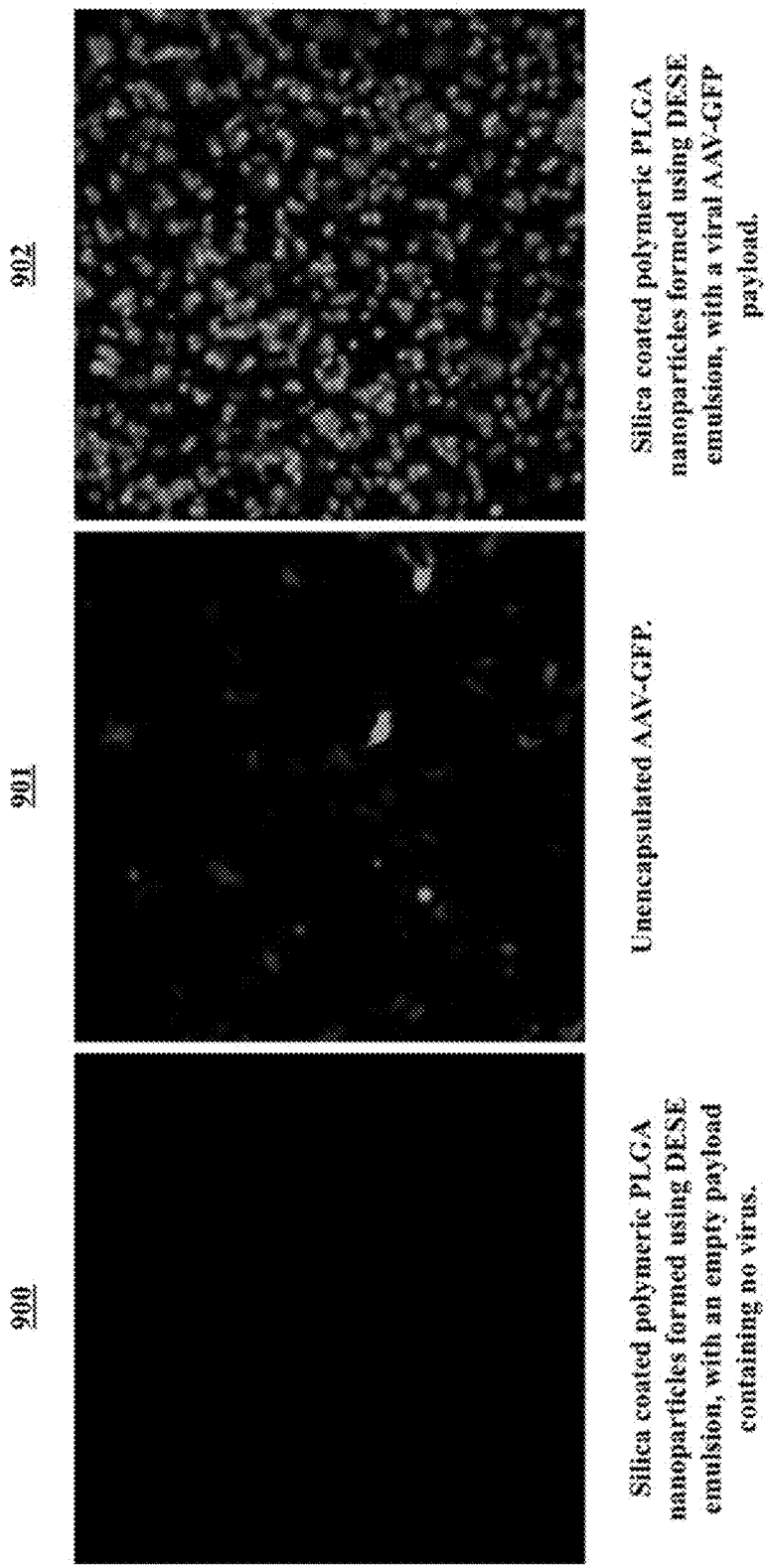
FIG. 9 shows fluorescence images of particles introduced to the environment host cells grown in culture. Fluorescence image (900) shows the result from delivering fabricated delivery vehicles comprising silica coated polymeric PLGA nanoparticles formed using a DESE emulsion step, and with an empty payload containing no virus. Fluorescence image (901) shows the result from delivering unencapsulated AAV-GFP virus, which expressed the green fluorescent protein GFP upon successful transduction. Fluorescence image (902) shows the result from delivering fabricated delivery vehicles comprising silica coated polymeric PLGA nanoparticles formed using a DESE emulsion step, and with a viral AAV-GFP payload. In this example, the delivery vehicles appear to have been transfected, the virus escaped the delivery vehicle after cell internalization, and GFP was successfully expressed.

FIG. 8 shows examples of a payload (801) within a delivery vehicle (800a-c) in accordance with some embodiments of the present disclosure. Delivery vehicle (800a) includes a nanoparticle, in this case polymeric nanoparticle (802) formed via an emulsion process, loaded with a payload, in this case enzyme (801), and an external structure, in this case porous coating (803). After administration to a subject, the delivery vehicle (800b) is exposed to small molecules (e.g. hydrogen peroxide, glucose) and immune system components (e.g. white blood cells, antibodies). In this case, delivery vehicle (800b) is exposed to a small molecule (e.g. 1-2 nm diameter) substrate (804) of enzyme (801), and to an immune system component (805) (e.g. antibody with 10-40 nm diameter). Substrate (804) is able to traverse into the delivery vehicle through porous coating (803), but immune system component (805) is too large to traverse porous coating (803). In some embodiments, as with delivery vehicle (800b), substrate (804) is able to pass into nanoparticle (802) and interact with enzyme (801) to result in small molecule product (806), which in turn is able to exit the delivery vehicle. In some embodiments. as with delivery vehicle (800c), the payload, in this case enzyme (801), is loaded onto the surface of nanoparticle (802), or escapes the nanoparticle (802), but is still encapsulated within porous coating (803) and unable to escape the delivery vehicle. Substrate (804) is able to enter delivery vehicle (800c) by traversing porous coating (803), and thereby interact with enzyme (801) to result in product (806). In some embodiments, a plurality of substances required for activity of payload (801) are able to traverse porous coating (803).

In some embodiments of the present disclosure, scanning electron microscopy (SEM), transmission electron microscopy (TEM), STEM, dynamic light scattering (DLS), or a combination thereof is used to characterized polymeric particle (106) and/or delivery vehicle (107) size, Zeta potential charge, or surface morphology.

Figure 2A:
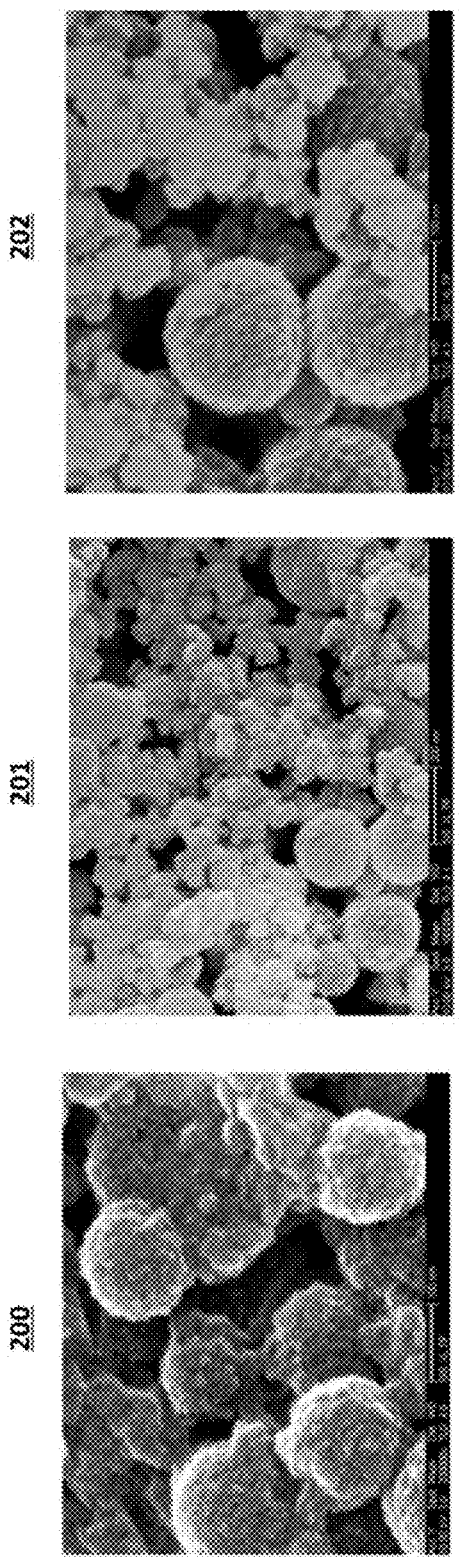
FIG. 2A shows SEM images (200, 201, 202) of fabricated delivery vehicles comprised of catalase loaded PLGA nanoparticles that are silica coated.

FIG. 2A shows images (200, 201, 202) generated by using SEM to analyze fabricated delivery vehicles comprised of catalase loaded PLGA nanoparticles that are silica coated. In this example, the median delivery vehicle particle size was approximately 100-120 nm in diameter. The fabricated delivery vehicles were also analyzed using DLS. In this example, the dispersity, or Poly Dispersity Index (PDI), was measured at 0.1-0.3. SEM was also used to successfully verify the formation of delivery vehicles comprised of silica coated PLGA nanoparticles with a payload of AAV virus.

Figure 2B:
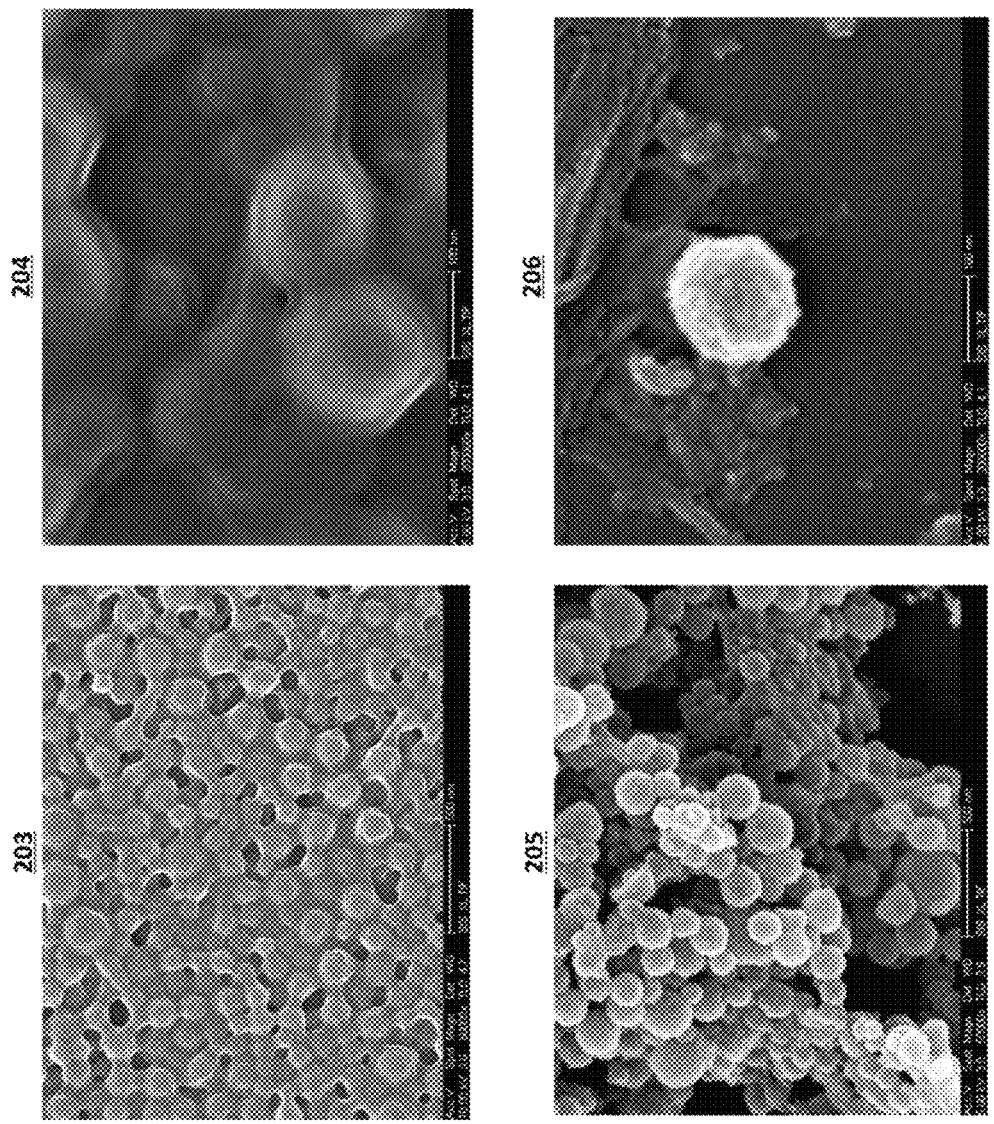
FIG. 2B shows SEM images of fabricated PLGA nanoparticles without a silica coating (203, 204), and images of delivery vehicles comprising PLGA nanoparticles coated with silica (205, 206).

FIG. 2B shows images generated by using an SEM to analyze fabricated PLGA nanoparticles without a silica coating (203, 204), and images of delivery vehicles comprising PLGA nanoparticles coated with silica (205, 206). In this example, SEM measurements show that uncoated PLGA nanocarriers were approximately between 100-200 nm in diameter, and the silica coated delivery vehicles were approximately between 100-300 nm. The samples were also analyzed using DLS. In this example, the measured PDI of the uncoated PLGA nanocarriers and the silica coated delivery vehicles were 0.174 and 0.271 respectively; the Zeta potentials were −19.0 mV and −25.6 mV respectively; and the Zeta average sizes were 239.3 nm and 318.7 nm respectively. In some embodiments, DLS and Zeta average size measures the hydrodynamic radius of the entities and may therefore overestimate the size with respect to SEM measurements. In some embodiments, residual PVA from the synthesis step may also amplify this effect.

Figure 3A:
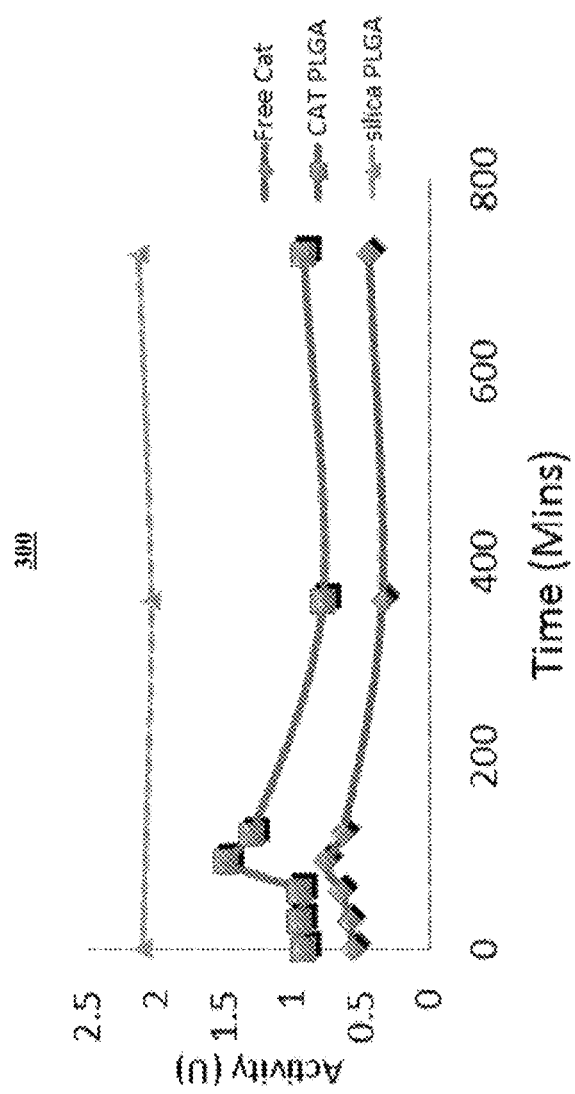
FIG. 3A shows graph (300) indicating catalase loaded PLGA nanoparticles have a burst release in the early time points, whereas delivery vehicles comprised of catalase loaded PLGA coated with silica maintains a higher and more stable activity at the experimented time points.

FIG. 3A shows graph (300) indicating that nanocarriers comprised of catalase loaded PLGA nanoparticles have a burst release in the early time points, whereas delivery vehicles comprised of catalase loaded PLGA coated with silica maintains a higher and more stable activity at the experimented time points.

Figure 3B:
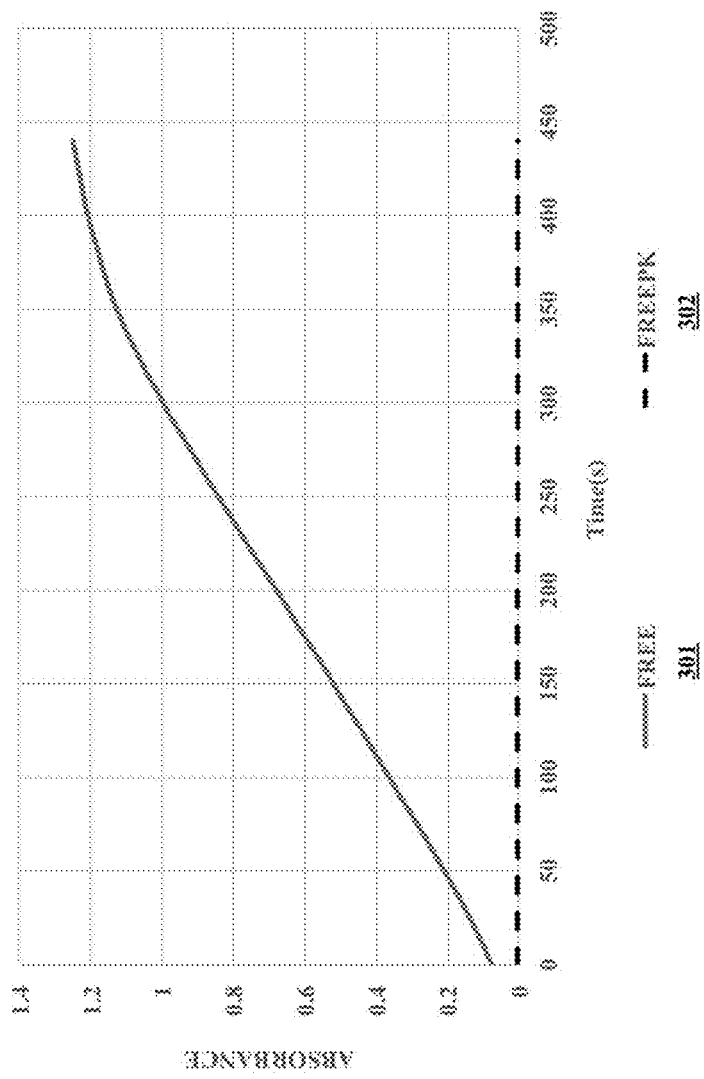
FIG. 3B shows measurements of Beta Lactamase (BLA) activity in the absence (301) and presence (302) of Proteinase-K (PK).

FIGS. 3B and 3C show examples of enzyme activity when the payload was the enzyme Beta Lactamase (BLA). To verify enzyme encapsulation and activity, three separate preparations were incubated with and without Proteinase-K (PK). PK is a serine protease that exhibits broad cleavage activity and will irreversibly cleave any BLA (i.e. stop its activity) that is not protected by encapsulation. In this example, the three preparations were exposed to Proteinase-K (Thermo Scientific Pierce Proteinase K) enzyme overnight at a concentration of 0.1 mg/ml in 1× phosphate buffered saline (PBS) solution at 37° C. Enzyme activity assay was done on the samples post incubation with PK using a Nitrocefin Assay (BLA hydrolysis of nitrocefin produces a shift of UV absorption inside the visible light spectrum from intact nitrocefin (~380 nm) to degraded nitrocefin (~500 nm) allowing visual detection of BLA activity on a macroscopic level). Each reaction was 100 μl in total and contained 250 μg/ml nitrocefin as substrate. Absorbance was measured at 486 nm. The resulting graph shows that bare unencapsulated enzyme (301) loses all activity when exposed to PK (302). Uncoated nanocarriers comprising BLA enzyme and PLGA nanoparticles (303) lose a significant portion of enzyme activity when exposed to PK (304). This is possibly due to initial burst release behavior of BLA from the PLGA nanoparticles. BLA within silica coated delivery vehicles (305) shows almost unchanged activity after PK treatment (306). The enzyme did not leak out of the delivery vehicle (where the PK is present). Furthermore, PK is not permitted to traverse into the delivery vehicle (where the enzyme is present). Therefore the payload was protected from PK, and by extrapolation, from other entities of similar or greater size that may inhibit payload bioactivity.

Advantageously, in some embodiments the delivery vehicle is administered to a subject for diagnostic applications, or therapeutic applications to treat a condition of the subject. Some examples of the conditions include but are not limited to cancer, pre-cancerous lesions, oxidative stress in ischemia and reperfusion injury, multiple sclerosis, gout, HIV infection, a condition requiring gene therapy, a condition requiring enzyme replacement therapy (e.g. Gaucher disease, Fabry disease, Hunter syndrome, Pompe disease), or a condition treatable with the introduction of foreign enzymes. In some embodiments, delivery vehicles are used for delivery of one or more biological, chemical or biochemical substances to facilitate, for example but not limited to, amino acid depletion therapy for cancerous tumors, other cancer therapy, antioxidant therapy for oxidative stress, modulating cellular gene expression, imaging (e.g. in the brain by using a fluorescent payload, or a quantum dot), bio-sensing, or a combination thereof.

In some embodiments, forming a nanoparticle includes an emulsion process to form a liposome.

Delivery Vehicle with Liposome

Liposomes are vesicles that are comprised of at least one lipid bilayer. Liposomes are limited in their capability as versatile delivery vehicles, particularly because they are detected and cleared by a subject's immune system and have a short circulation half-life. In one aspect, disclosed herein is the ability to preserve and deliver a payload loaded in a liposome with significantly enhanced preservation and delivery properties, for example reduced immunogenicity, less rapid clearance, and longer circulation half-life. In some embodiments, also disclosed herein is the ability to preserve activity or externally trigger activity of an active or bioactive payload using this novel delivery vehicle comprising a coated loaded liposome.

In one aspect, the present disclosure provides a system and method for delivering and preserving a payload in a subject comprising the steps of: (i) forming a nanoparticle encapsulating the payload, wherein the nanoparticle comprises a liposome, and wherein the payload is a biological, chemical or biochemical substance; (ii) coating the nanoparticle with a biocompatible coating to form a delivery vehicle; and (iii) administering the delivery vehicle to the subject, wherein upon administration at least one of the following properties is enhanced relative to administering an uncoated nanoparticle: (a) preservation from cell-mediated or antibody immune response; (b) reduced toxicity; (c) half-life of the payload (e.g. in circulation); (d) utilization of the payload, or (e) cellular uptake of the payload. In some embodiments, at least one of the above properties is enhanced relative to administering an unencapsulated payload.

In some embodiments of the present disclosure, the structural integrity of the liposome within the delivery vehicle described above is purposefully disrupted while the coating and payload remain intact, such as for example but not limited to, by applying sonication or ultrasound to the delivery vehicle. In some embodiments, the activity of the payload is externally controllable by disrupting the inner liposome at a target site within a subject by applying or focusing sufficient ultrasound power at or near the target site. In some embodiments where the payload is an enzyme and the coating is porous, the internal liposome structure is broken up to facilitate substrates and products to diffuse to and from the payload, while the enzyme remains caged within the porous coating of the delivery vehicle as it is unable to traverse the porous coating. In some embodiments, the ultrasound used to disrupt the liposomes is generated by medical diagnostic ultrasound or therapeutic grade ultrasound equipment. Those skilled in the art will know numerous ultrasound devices, including for example the Toshiba Aplio Platinum System, Philips EPIQ, GE LOGIQ or GE Vivid. In some embodiments, ultrasound applied in the 1 MHz-1.5 MHz range is sufficient to break apart liposomes. Additionally, delivery vehicles fabricated using the above process were imaged using SEM imaging before and after the application of ultrasound in the same frequency. It was also verified that the silica coating of the delivery vehicles remains unbroken.

In some embodiments of the present disclosure, the liposome is unilamellar (UV), small unilamellar (SUV), medium unilamellar (MUV), large unilamellar (LUV), or multi vesicular (MV).

In some embodiments, the liposome is loaded with a hydrophobic and/or hydrophilic payload. In one embodiment, the payload comprises a virus, virus-like particle (VLP), a virus protein capsid, or a combination thereof. In some embodiments, the payload comprises a natural virus, recombinant virus, or engineered virus. In some embodiments, the payload comprises a nucleic acid, such as for example DNA, RNA, siRNA, or a combination thereof. Additionally, in an embodiment wherein the payload comprises a nucleic acid or virus (or VLP), the delivery vehicle is used to transform or transfect a host cell in the subject.

In some embodiments of the present disclosure, the liposome is fabricated using an emulsion process, for example but not limited to using a reverse phase evaporation method. In an embodiment, lipid organic solvent and aqueous solution are mixed, sonicated. A water/oil emulsion is formed, after which the organic solvent is removed using evaporation. The lipids form a phospholipid bilayer, on vigorous shaking, water droplets collapse and formation of liposomes takes place. In some embodiments, phosphocholine is used as the liposome backbone.

In some embodiments, the liposome is loaded with payload passively (e.g. the payload is encapsulated during liposome formation), or actively (after liposome formation, e.g. by employing a pH gradient).

In some embodiments of the present disclosure, the charge of the liposome is modulated to facilitate the external coating step. A positively charged (cationic) liposome will facilitate coating of surface with silica or calcium phosphate. In some embodiments, the liposomal nanoparticles are synthesized with approximately +10 mV to +15 mV change to facilitate coating with silica. The charge difference facilitates tetramethyl orthosilicate (TMOS) to preferentially precipitate from solution as silica on the liposome surface. In some embodiments, the liposome nanoparticle is synthesized at least partially using a composition including a cationic analog of phosphocholine, such as for example but not limited to 1,2-dioleoyl-3-trimethylammonium-propane (DOTAP). In some embodiments, the liposome formulation comprises of DOTAP, phosphocholine, cholesterol, and PEG-lipid. In some embodiments, the inclusion of DOTAP and/or PEG reduces the particle aggregation. In some embodiments, an anionic liposome is synthesized, for example, to facilitate polymer coating.

Figure 4:
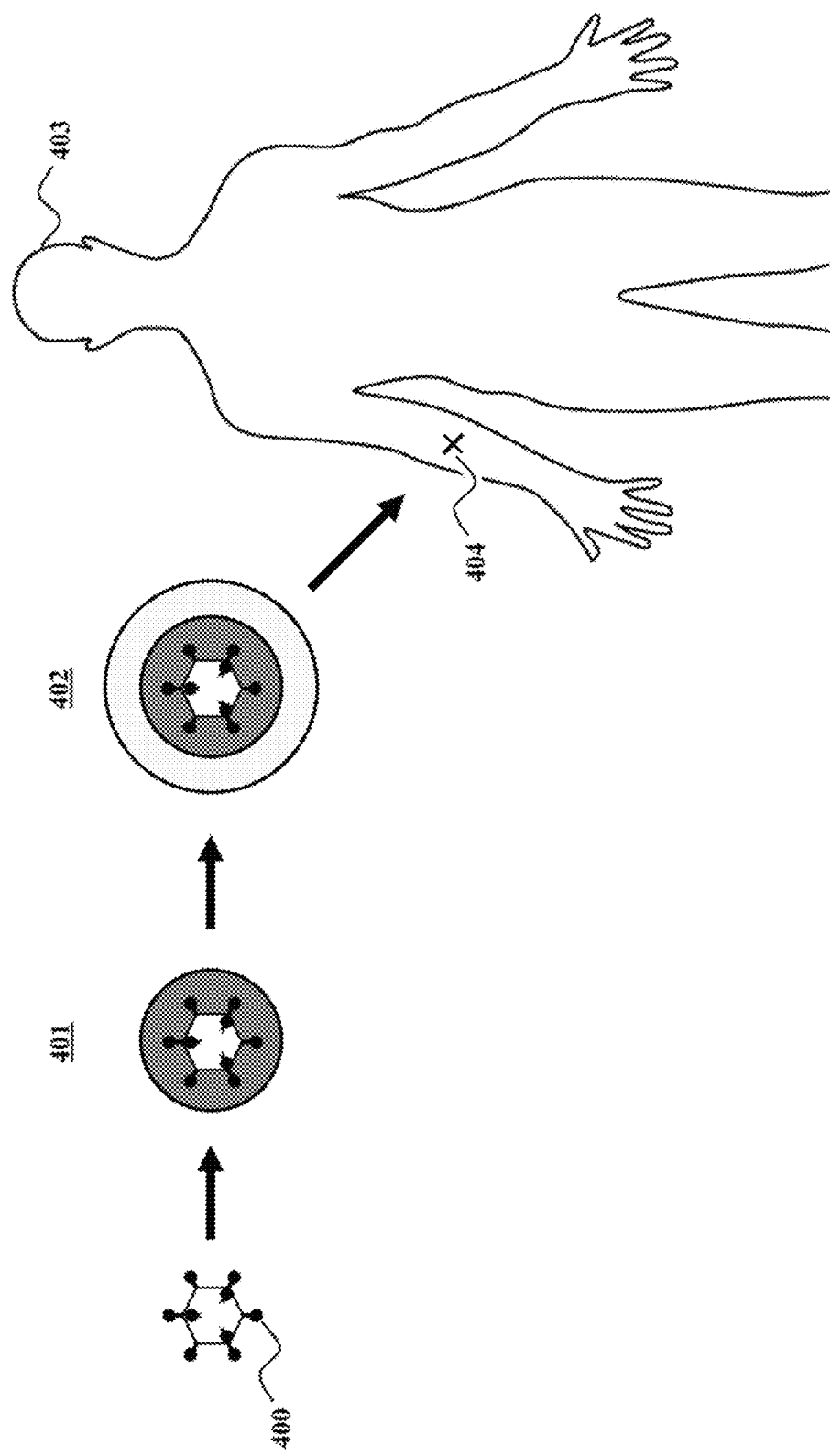
FIG. 4 shows an example of a method for fabricating encapsulation of a virus (400), in accordance with an embodiment of the present disclosure.

FIG. 4 shows an example of a method for encapsulating virus (300), in accordance with an embodiment of the present disclosure. In this example, virus (300) is an oncolytic adenovirus or AAV. A nanocarrier (301) is prepared by encapsulating virus (300) within a liposome. Delivery vehicle (302) is then formed by coating nanocarrier (301) with a coating. In this example, the liposomal nanocarrier (301) particle is coated with silica. Delivery vehicle (302) is then administered to subject (303) via administration site (304). In this case, delivery vehicle (302) is administered using an injection, such as, for example but not limited to, subcutaneous injection, intratumoral injection, intramuscular injection, intravenous injection, other extracellular injection, or a combination thereof. In some embodiments of the present disclosure, scanning electron microscopy (SEM), transmission electron microscopy (TEM), STEM, dynamic light scattering (DLS), or a combination thereof is used to characterized nanocarrier (301) or delivery vehicle (302) size or surface morphology.

Referring to FIG. 8, payload (811) is encapsulated within a delivery vehicle (810a-d) in accordance with some embodiments of the present disclosure. Delivery vehicle (810a) includes a nanoparticle, in this case a liposome (812), loaded with a payload, in this case enzyme (811), and an external structure, in this case porous coating (813). After administration to a subject, the delivery vehicle (810b) is exposed to small molecules (e.g. hydrogen peroxide, glucose) and immune system components (e.g. white blood cells, antibodies). In this case, delivery vehicle (810b) is exposed to a small molecule (e.g. 1-2 nm diameter) substrate (814) of enzyme (811), and to an immune system component (815) (e.g. antibody with 10-40 nm diameter). Immune system component (815) is too large to traverse porous coating (803). Substrate (814) also cannot enter delivery vehicle (810b) to interact with enzyme (811) as it cannot traverse into liposome (812). In some embodiments, delivery vehicle (800c) is exposed to external control, in this case ultrasound vibrations (816), within the subject (e.g. in-vivo via an ultrasound probe or transducer in contact with the subject). Ultrasound vibration disrupt the integrity of liposome (812), resulting in a delivery vehicle (800c) with undamaged porous coating (813) but without an intact liposome (812). Now substrate (814) is able to traverse into the delivery vehicle (810d), interact with the enzyme (811), and result in a product (817). Immune component (815) remains unable to traverse porous coating (813). In some embodiments, ultrasound vibrations (816) are applied to delivery vehicle (810a) before it is administered to the patient (ex-vivo). In some embodiments, a plurality of substances required for activity of payload (811) are able to traverse porous coating (813).

In some embodiments of the present disclosure, wherein the loading efficiency is below 100%, at least some of the remaining unencapsulated payload is recovered and re-used, for example, in a subsequent encapsulation procedure.

In some embodiments of this patent document, variations to this fabrication method may be used depending on the specific payload and/or intended application. Methods of forming loaded liposomes will be known to those familiar in the art. Examples of variations that can be modified include, but are not limited to: payload, chemicals, particle size, silica coating time, sonication duration and/or power, surface coating surface modification, or a combination thereof.

In some embodiments, the delivery vehicle is fabricated by synthesizing liposomes by the reverse phase evaporation process, and subsequently coating them. In one embodiment, the coating is a nanoscale layer of silica applied using a sol-gel chemistry. In an embodiment, silica coating is by using Silicic acid, which is a highly reactive hydrolyzed silicon hydroxide molecule which tends to precipitate on cationic surface to form a hydrophilic sol-gel layer. In some embodiments wherein the payload is an enzyme, this method above ensures that the enzyme remains active inside the delivery vehicle, in spite of lack in reactivity of the liposomes and quick internalization by macrophages. The enzymes/proteins are unmodified and retain similar activity in the silica coated liposomes to uncoated liposomes.

Figure 5:
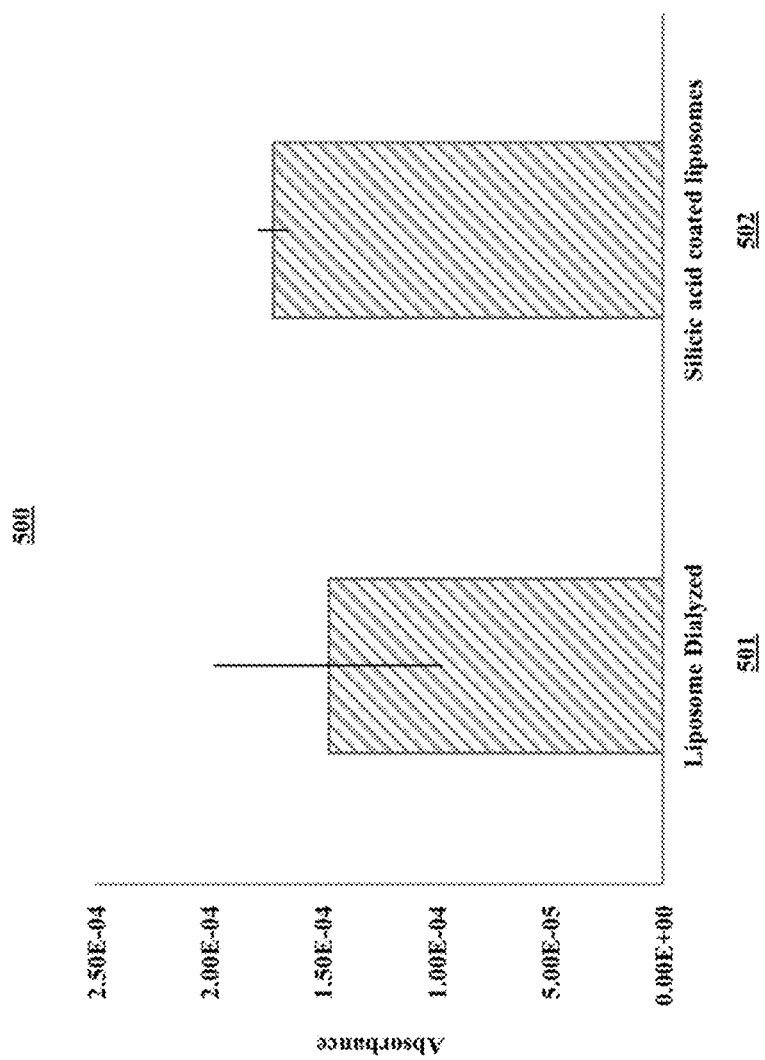
FIG. 5 shows an example of enzyme activity (500) when the payload is the enzyme Beta Lactamase (BLA). BLA activity is similar within uncoated dialyzed liposomes (501) and delivery vehicles comprising silicic acid coated liposomes (502).

FIG. 5 shows an example of enzyme activity (500) when the payload was the enzyme Beta Lactamase (BLA). Enzyme activity assay was done on the samples using a Nitrocefin Assay (BLA hydrolysis of nitrocefin produces a shift of UV absorption inside the visible light spectrum from intact nitrocefin (~380 nm) to degraded nitrocefin (~500 nm) allowing visual detection of BLA activity on a macroscopic level). BLA activity was similar within uncoated dialyzed liposomes (501) and delivery vehicles comprising silicic acid coated liposomes (502). The samples were also analyzed using DLS. In this example, the measured PDI of the uncoated liposome nanocarriers and the silica coated liposome delivery vehicles were 0.156 and 0.297 respectively; the Zeta potentials were +15.2 mV and −23.4 mV respectively; and the Zeta average sizes were 204.8 nm and 356.6 nm respectively.

Figure 6:
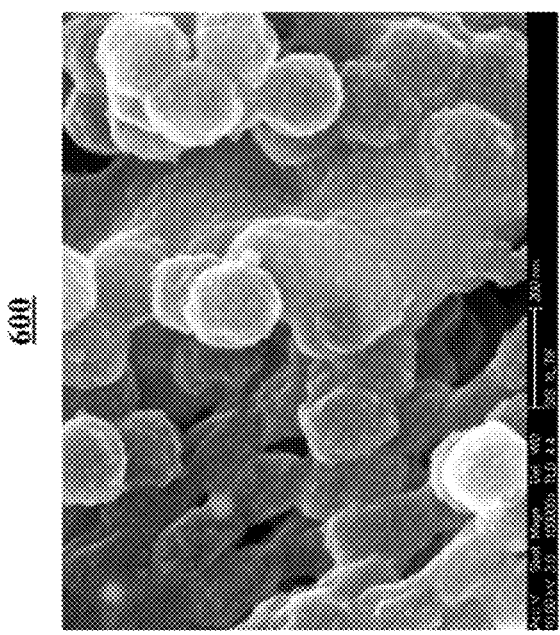
FIG. 6 shows an SEM image of fabricated delivery vehicles comprising liposome nanoparticle coated with silica (600).

FIG. 6 shows an SEM image of fabricated delivery vehicles that comprised of liposome nanocarriers coated with silica (600).

Delivery of Grouped Payload

In one aspect, disclosed herein is a system and method to deliver and preserve activity or bioactivity in a subject of a group of interacting biological, chemical or biochemical substances comprising the steps of (i) forming a porous layer encapsulating the group to form a delivery vehicle, (ii) administering the delivery vehicle to the subject, wherein upon administration at least one of the following properties is enhanced relative to administering at least one of the substances without encapsulation: (a) preservation from cell-mediated or antibody immune response; (b) reduced toxicity; (c) half-life of the substances (e.g. in circulation); (d) utilization of the substances, or (e) cellular uptake of the substances.

For example, the disclosure provides a system and method to delivery and preserve activity or bioactivity in a subject of a group of interacting biological, chemical or biochemical substances comprising the steps of (i) forming a nanoparticle encapsulating a payload (e.g. loaded polymeric nanoparticle, loaded liposome, etc.), wherein the payload is a group of interacting biological, chemical or biochemical substances, (ii) coating the nanoparticle with a biocompatible porous coating to form a delivery vehicle; and (iii) administering the delivery vehicle to the subject, wherein upon administration the group is prevented from traversing the porous coating, and wherein at least one additional substance essential for the activity or bioactivity is permitted to traverse the porous coating to or from the active or bioactive payload, and wherein at least one of the following properties is enhanced relative to administering uncoated nanoparticle: (a) preservation from cell-mediated or antibody immune response; (b) reduced toxicity; (c) half-life of the active or bioactive payload (e.g. in circulation); or (d) utilization of the active or bioactive payload. In some embodiments, at least one of the above properties is enhanced relative to administering at least one of the biological, chemical or biochemical substances without encapsulation. In some embodiments, the nanoparticle is formed using an emulsion process or step (emulsification) wherein the biological, chemical or biochemical substances are not bound to the nanoparticle, such as for example a polymeric nanoparticle formed using double-emulsion-solvent-evaporation (DESE), or a liposomal particle. In some embodiments, at least one of the group of biological, chemical or biochemical substances is loaded or absorbed into the coating of the delivery vehicle.

In some embodiments of the present disclosure, interacting substances are substances with at least one direct interaction, indirect interaction, dependency, synergistic effect, reliance on same input or substrate, sequential activity, or cascading activity. In one embodiment, the interacting biological, chemical or biochemical substances are cascading enzymes or part of at least a portion of an enzymatic cascade (e.g. sequential enzymes and/or cofactors). An initial stimulus triggers a sequence of reactions, whereby the product of a preceding reaction is consumed in the next reaction. In some embodiments, a bioactive enzymatic cascade is encapsulated within a delivery vehicle (e.g. sonicated silica-coated liposome; silica-coated PLGA nanoparticle formed using DESE or nano-precipitation) with the purpose of detecting an extracellular or intracellular biological, chemical or biochemical substance in a subject, for example but not limited to, a human, mammal, model organism or other animal. In one experiment, an enzymatic cascade was used to detect acetylcholine, in accordance with an embodiment (e.g. can be used to investigate, for example but not limited to, neuromuscular junctions). Acetylcholine could be used as an early biomarker for leukemia. The enzymatic cascade was comprised of acetylcholinesterase (ACHE, acetylhydrolase), choline oxidase (CHOX), and horseradish peroxidase (HRP). ACHE is an enzyme that catalyzes the hydrolysis of acetylcholine to acetate and choline. CHOX is an enzyme that catalyzes choline and oxygen into betaine aldehyde and hydrogen peroxide. HRP is an enzyme that is used in applications for its ability to amplify a weak signal and/or increase detectability of a target molecule. A number of different HRP substrates are commercially available to exploit such properties of HRP. In accordance with an embodiment, luminol was used as the substrate. Hydrogen peroxide oxidizes luminol to produce aminophthalic acid, nitrogen gas, water, and emits light, which can be detected. In accordance with an embodiment, Amplex Red was used as the substrate. Amplex Red reagent, in combination with HRP, is used to detect hydrogen peroxide generated in the above enzyme-couple reactions. A red-fluorescent oxidation product, resorufin, is produced that has excitation maxima and emission maxima of approximately 571 nm and 585 nm respectively. This reaction has been used to detect as little as 10 pmol of hydrogen peroxide in a 100 μL volume or 10-5 U/mL of HRP. In accordance with an embodiment, the enzyme catalase was used to catalyze the decomposition of hydrogen peroxide to oxygen and water, wherein the oxygen is detected using ultrasound imaging technology.

Figure 7:
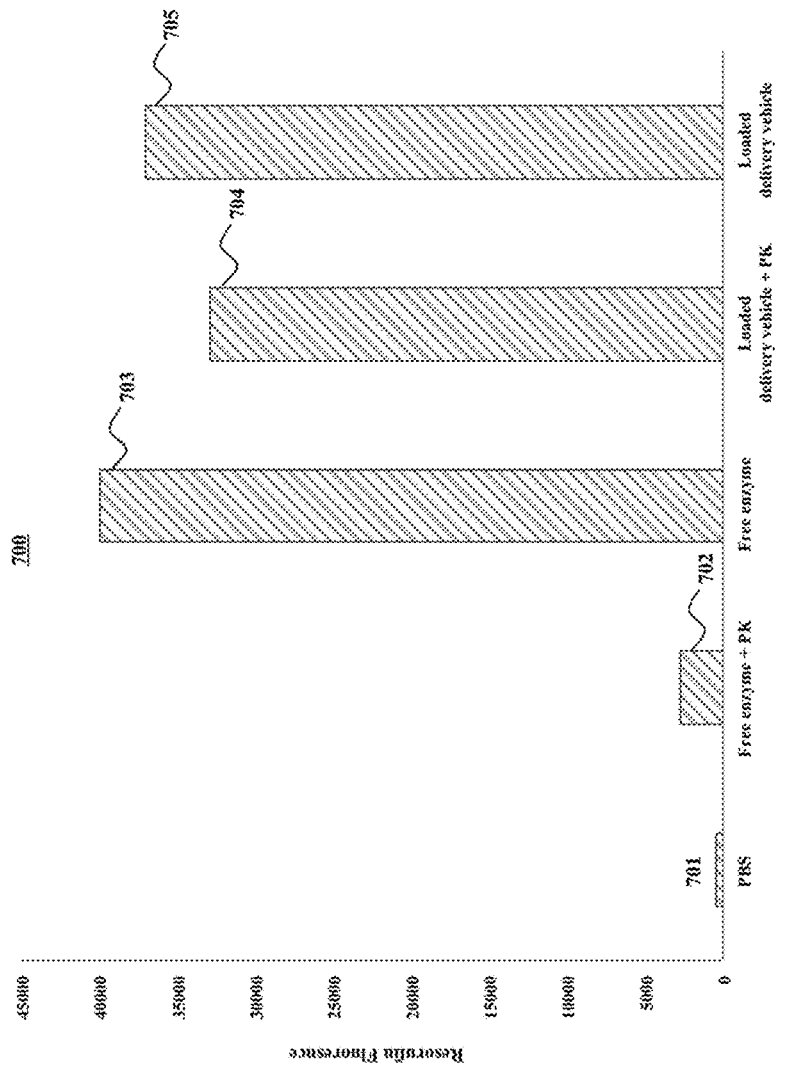
FIG. 7 shows the results of measuring resorufin fluorescence levels (700) when the payload was an enzymatic cascade comprising ACHE, CHOX, HRP and Amplex Red. Fluorescence is determined by the rate of the above enzyme reactions, including conversion of Amplex Red to resorufin in the presence of hydrogen peroxide and HRP. The delivery vehicles were comprised of silica coated liposomes that encapsulate the payload.

FIG. 7 shows the results of measuring resorufin fluorescence levels (700) when the payload was an enzymatic cascade comprising ACHE, CHOX, HRP and Amplex Red. Fluorescence is determined by the rate of the above enzyme reactions, including conversion of Amplex Red to resorufin in the presence of hydrogen peroxide and HRP. To verify enzyme encapsulation and activity, three separate preparations were incubated with and without Proteinase-K (PK). PK is a serine protease that exhibits broad cleavage activity and will irreversibly cleave any enzyme (i.e. stop its activity) that is not protected by encapsulation. The resulting graph (700) shows results where significant fluorescence was observed with a preparation comprising control phosphate-buffered saline (PBS) solution (701). High activity was observed with bare unencapsulated enzymes (703), which was lost when the enzymes are exposed to PK (702). Similarly high activity was observed (705) when a delivery vehicle encapsulated the payload, wherein the delivery vehicles were comprised of silica coated liposomes that encapsulated the cascading enzymes. This activity was not significantly compromised by exposure to PK (704).

In one aspect, the present disclosure provides a system and method to deliver a payload to an organ, tissue or cell of a subject comprising the steps of (i) forming a nanoparticle encapsulating a payload (e.g. loaded polymeric nanoparticle, loaded liposome, etc.), wherein the payload is a plurality of viruses, (ii) coating the nanoparticle with a biocompatible coating to form a delivery vehicle; and (iii) administering the delivery vehicle to the subject, wherein any one delivery vehicle that subsequently enters a cell in the subject will contemporaneously deliver a plurality of viruses to the cell, and wherein upon administration at least one of the following properties is enhanced relative to administering uncoated nanoparticle: (a) preservation from cell-mediated or antibody immune response; (b) reduced toxicity; (c) half-life of the payload (e.g. in circulation); (d) utilization of the payload, or (e) cellular uptake of the payload. In some embodiments, at least one of the above properties is enhanced relative to administering at least one of the viruses without encapsulation. In some embodiments, the nanoparticle is formed using an emulsion process wherein the viruses are not bound to the nanoparticle, such as for example a polymeric nanoparticle formed using double-emulsion-solvent-evaporation (DESE), or a liposomal particle.

In one aspect, the present disclosure provides a system and method to enhance a virus-induced response in a subject, comprising administering to the subject a delivery vehicle, wherein the delivery vehicle encapsulates a plurality of viruses, and, if structural integrity of the delivery vehicle is compromised, such as within the high acidity (low pH) of a cellular compartment (e.g. endosome after cellular internalization), the plurality of viruses are contemporaneously released. In some embodiments of the present disclosure, the multiple viruses are dependent or work synergistically to, for example but not limited, deliver CRISPR/Cas9 genome editing, treat a condition by modulating multiple genes or genetic loci in the subject, produce multiple proteins or products within cells, or a combination thereof. In some embodiments wherein the co-encapsulation of a plurality of viruses in a nanoparticle is a stochastic process (e.g. using a DESE emulsion with the viruses in the first water phase), then the nanoparticles need to be created of sufficient size to statistically capture the effective amount composition of viruses per delivery vehicle. As disclosed above, changes in the DESE process conditions were used to control nanoparticle size.

Currently in vivo CRISPR/Cas9 genome editing applications have limitations, for example problems with Cas9 delivery. While viral vectors such as AAV can be used, there are numerous problems due their immunogenicity/immune clearance (particularly on repeat administrations), tropism, and notably challenges due to low genetic packaging capacity (particularly for AAV). In one aspect, the present disclosure provides a system and method to be able to deliver multiple viral vectors simultaneously in a single delivery vehicle, wherein Cas9 and multiple gRNAs are separately packaged into the multiple vectors. This disclosure therefore enhances the total genetic packaging capacity and facilitates co-infection of the multiple vectors.

Advantageously, simultaneously delivering more than one functional viruses into a cell using this method can have an enhanced effect on infection/transduction success and expression. The in vitro cell line infection experiments have demonstrated that there is an unexpected non-linear relationship between quantity of viruses per delivery vehicle and the subsequent rate of infection. In some embodiments, the plurality of viruses are delivered using the uncoated loaded nanoparticle (e.g. polymeric nanoparticle formed using an emulsion process). In some embodiments, the plurality of viruses belong to the same serotype, species, genus or family. In some embodiments, the plurality of viruses comprise a mixture of different natural viruses, engineered viruses, or a combination thereof.

Modifications and Variations

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

Some present embodiments have been described in connection with one or more peptides, enzymes, drugs or viruses. In general, devices and technology disclosed herein can be applied to other natural, engineered or recombinant viruses, or other biological entities, as well.

Some present embodiments have been described in connection with polymeric nanoparticle or nanocarrier fabrication techniques, such as DESE or nano-precipitation. In general, devices and technology disclosed herein can be applied to polymeric nanoparticles manufactured using other methods, or to non-polymeric nanoparticles or nanocarriers. Some present embodiments have been described in connection with encapsulation. In general, devices and technology described herein can be applied with partial or substantial encapsulation.

In some embodiments, delivery vehicles are used for circulatory applications, other extracellular applications, intracellular applications, or a combination thereof.

None of the description in the present patent document should be read as implying that any particular element, step, or function is an essential element which must be included in the claim scope.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the contact of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A delivery device for delivering a biological, chemical or biochemical substance to a subject comprising:
   a biocompatible coating structure with a pore size that is at least semipermeable by a substrate;
   a liposome, positioned inside the biocompatible coating structure, including an internal structure that is disrupted by applying ultrasound such that the substrate diffuses through the disrupted internal structure of the liposome; and
   a payload located in the internal structure of the liposome, wherein the payload includes an enzymatic cascade and an additional substance for activity of the payload, wherein the enzymatic cascade includes acetylcholinesterase (ACHE), choline oxidase (CHOX), and horseradish peroxidase (HRP),
   wherein the biocompatible coating structure and the payload are structured to remain intact when the internal structure of the liposome is disrupted by applying ultrasound, and wherein, after the liposome is disrupted, the additional substance traverses the biocompatible coating structure and the enzymatic cascade does not traverse the biocompatible coating structure.

2. The delivery device of claim 1, wherein after the liposome is disrupted, the enzymatic cascade maintains activity within the delivery device.

3. The delivery device of claim 1, further comprising functionalization molecules on the surface of the biocompatible coating structure for modulating a biodistribution of the delivery device within the subject.

4. The delivery device of claim 1, wherein the biocompatible coating structure comprises a porous layer including silica, calcium phosphate, or titanium oxide.

5. The delivery device of claim 1, wherein the payload is released if the delivery device is internalized within a cell.

6. The delivery device of claim 1, wherein the pore size is 1-9 nanometers.

7. The delivery device of claim 4, wherein the porous layer comprises 20% to 100% of the silica, the calcium phosphate, or the titanium oxide.

8. The delivery device of claim 1, wherein an immune system response protection of a patient is enhanced compared to an uncoated liposome.

9. The delivery device of claim 1, wherein a circulation half-life in a patient of the biological, chemical or biochemical substance is enhanced compared to an uncoated liposome.

10. The delivery device of claim 1, wherein a payload utilization is enhanced compared to an uncoated liposome.

11. The delivery device of claim 1, wherein a toxicity is reduced compared to an uncoated liposome.

12. The delivery device of claim 1, wherein a cellular uptake is enhanced compared to an uncoated liposome.

13. The delivery device of claim 1, wherein the internal structure of the liposome is disrupted by an ultrasonic device producing ultrasonic energy at one or more frequencies between 1 MHz and 1.5 MHz.

14. The delivery device of claim 1, wherein the liposome comprises:
 1,2-dioleoyl-3-trimethylammonium-propane (DOTAP);
 phosphocholine;
 cholesterol, and
 polyethylene glycol (PEG).

15. The delivery device of claim 1, wherein the enzymatic cascade further comprises Amplex Red.

* * * * *